United States Patent [19]

Budnick

[11] Patent Number: 4,579,720

[45] Date of Patent: Apr. 1, 1986

[54] CHELATION

[75] Inventor: Edward G. Budnick, Scotch Plains, N.J.

[73] Assignee: Plains Chemical Development Co., Scotch Plains, N.J.

[21] Appl. No.: 539,562

[22] Filed: Oct. 6, 1983

Related U.S. Application Data

[60] Division of Ser. No. 149,833, Jun. 3, 1971, Pat. No. 4,440,646, and a continuation-in-part of Ser. No. 482,257, Aug. 24, 1965, Pat. No. 3,471,552, and a continuation-in-part of Ser. No. 818,802, Apr. 23, 1969, Pat. No. 3,892,676, which is a division of Ser. No. 485,624, Sep. 7, 1965, Pat. No. 3,471,406, and a continuation-in-part of Ser. No. 813,385, Feb. 27, 1969, abandoned, which is a division of Ser. No. 505,471, Oct. 28, 1965, abandoned.

[51] Int. Cl.$^4$ .............................................. C07F 7/22
[52] U.S. Cl. ...................................... 423/10; 423/24; 423/253; 423/254; 423/256; 423/260; 260/501.21; 260/502.4 P; 252/135; 252/DIG. 11; 534/11; 556/18
[58] Field of Search .................. 423/24, 253, 254, 256, 423/260, 10; 260/429.1, 430, 502.4 P, 501.21; 252/135

[56] References Cited

U.S. PATENT DOCUMENTS

| | | | |
|---|---|---|---|
| 3,471,406 | | Budnick | 252/135 |
| 3,471,552 | 10/1969 | Budnick | 260/502.4 P |
| 3,904,493 | 9/1975 | Lori et al. | 260/502.4 P |
| 4,020,091 | 4/1977 | Budnick | 260/502.4 P |

*Primary Examiner*—Paul Lieberman
*Assistant Examiner*—Hoa Vance
*Attorney, Agent, or Firm*—Cushman, Darby & Cushman

[57] ABSTRACT

Hydroxymethane diphosphonic acid and alkali metal or ammonium salt of such acid are prepared. They are useful in detergent compositions and in sequestering and chelating polyvalent metals.

17 Claims, No Drawings

CHELATION

The present application is a division of application Ser. No. 149,833, filed June 3, 1971, now U.S. Pat. No. 4,440,646 and a continuation-in-part of application Ser. No. 482,257 filed Aug. 24, 1965 and also is a continuation-in-part of application Ser. No. 818,802 filed Apr. 23, 1969, which is a division of application Ser. No. 485,624, filed Sept. 7, 1965 now U.S. Pat. No. 3,471,406 and is also a division of application Ser. No. 149,833, filed June 3, 1971, now U.S. Pat. No. 4,440,646 and a continuation-in-part of application Ser. No. 813,385 filed Feb. 27, 1969 which is a division of application Ser. No. 505,471 filed Oct. 28, 1965. There is nothing in the present application not found in either application Ser. Nos. 485,624 or 505,471.

This invention relates to the novel detergent compositions, chelating polyvalent metals and to novel polyphosphonic acids and salts thereof.

It has been proposed in the past to employ methane disphosphonic acid and its alkali metal salts in detergent compositions (Orthner, German Pat. No. 1,045,373, Dec. 4, 1958). Unfortunately, however, methane diphosphonic acid and its salts are relatively expensive to produce. While methane diphosphonic acid is a good builder and calcium sequestering agent, these properties can be improved upon. It is also desirable to have increased solubility in the sequestering agent.

It is an object of the present invention to prepare improved detergent compositions.

Another object is to prepare detergent compositions containing a phosphorus compound having a greater binding power for calcium ions than either alkali metal pyrophosphates or alkali metal tripolyphosphates.

An additional object is to prepare detergent compositions containing polyphosphates having a reduced tendency to revert to phosphoric acid.

Another object is to develop detergent compositions containing phosphonates superior to methane disphosphonic acid and its salts as sequestering agents for calcium ions.

A further object is to prepare phosphonate containing detergent compositions having improved stability.

Yet another object is to prepare detergent compositions having improved ability to remove sebum stains.

A still further object is to prepare phosphonate containing detergent compositions wherein the phosphonate has a lower surface tension than methane diphosphonic acid and its salts.

It is an additional object to provide novel sequestering agents.

Another object is to provide improved chelating agents with higher solubility and larger chelating capacity.

Another object is to chelate relatively insoluble ions.

A further object is to develop a novel process for the recovery of valuable metals from solutions by chelation.

Another object is to prepare detergent compositions containing alkali metal phosphonates more nearly neutral than the alkali metal salts of methane diphosphonic acid.

Still further objects and the entire scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

It has now been found that these objects can be attained by employing detergent compositions containing polyphosphonic acids and/or alkali metal and ammonium salts thereof having one of the formulae

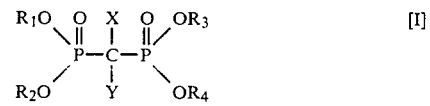

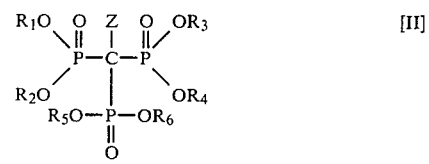

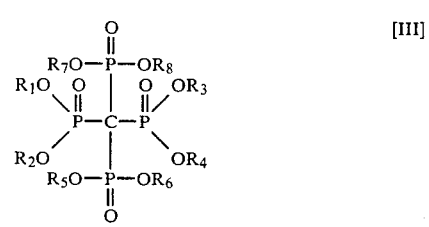

where $R_1$, $R_2$, $R_3$, $R_4$, $R_5$, $R_6$, $R_7$, and $R_8$ are the same or different and are selected from the group consisting of hydrogen, alkali metal (e.g., sodium, potassium, lithium, rubidium or cesium) or ammonium; X is selected from the group consisting of hydrogen, alkyl, alkenyl, chlorine, bromine, aryl (e.g., phenyl or alkylphenyl), chloroalkyl or chloroaryl (e.g., chlorophenyl); Y is selected from the group consisting of hydroxyl, phenyl, chlorine and bromine and Z is selected from the group consisting of phenyl, hydrogen, chlorine and bromine.

Examples of phosphonic acids and their salts useful in the detergent compositions of the present invention are chloromethane diphosphonic acid, dichloromethane diphosphonic acid, bromomethane diphosphonic acid, dibromomethane diphosphonic acid, chloromethane triphosphonic acid, bromomethane triphosphonic acid, methane triphosphonic acid, methane tetraphosphonic acid, hydroxymethane diphosphonic acid, methyl hydroxymethane diphosphonic acid (also called methyl hydroxymethylene diphosphonic acid or 1-methyl-1-hydroxymethane diphosphonic acid), ethyl hydroxymethane diphosphonic acid, butyl hydroxymethane diphosphonic acid, propyl hydroxymethane diphosphonic acid, isopropyl hydroxymethane diphosphonic acid, pentyl hydroxymethane diphosphonic acid, hexyl hydroxymethane diphosphonic acid, heptyl hydroxymethane diphosphonic acid, isoheptyl hydroxymethane diphosphonic acid, octyl hydroxymethane diphosphonic acid, nonyl hydroxymethane diphosphonic acid, decyl hydroxymethane diphosphonic acid, undecyl hydroxymethane diphosphonic acid, dodecyl hydroxymethane diphosphonic acid, tridecyl hydroxymethane diphosphonic acid, tetradecyl hydroxymethane diphosphonic acid, pentadecyl hydroxymethane diphosphonic acid, heptadecyl hydroxymethane diphosphonic acid, octadecyl hydroxymethane diphosphonic acid, nonadecyl hydroxymethane diphosphonic acid, heptadecenyl hydroxymethane diphosphonic acid, vinyl hydroxymethane diphosphonic acid, isopropenyl hydroxymethane diphosphonic acid, chloromethyl hydroxymethane diphosphonic acid, dichloromethyl hydroxymethane diphosphonic acid, trichloromethyl hydroxymethane diphosphonic acid, phenyl hydroxymethane diphosphonic acid, phenyl methane diphosphonic acid, phenyl methane triphosphonic acid, naphthyl hydroxy methane diphosphonic acid, p-chlorophenyl hydroxy methane diphosphonic acid, 2, 4, 5-trichlorophenyl hydroxy methane diphosphonic acid, 2, 4, 6-trichlorophenyl hydroxy methane diphosphonic acid, isononyl hydroxy methane diphosphonic acid and the alkali metal and ammonium salts of such phosphonic acids.

Since the phosphonic acids used in the present invention have 4, 6 or 8 acidic hydrogen atoms (Formulae I, II and III respectively) in making the salts one or more of the acidic hydrogen atoms can be replaced by the alkali metal or ammonium ion in forming the salts. Usually all of the acidic hydrogen atoms are replaced in making the salts and unless otherwise indicated when reference is made to a salt in the present specification, all of the acidic hydrogen atoms are replaced. However, it should be understood that this is not an essential part of the present invention and the invention includes the use of the partial as well as the complete salts, e.g., monosodium methane tetraphosphonate, disodium methane tetraphosphonate, trisodium methane tetraphosphonate, tetrasodium methane tetraphosphonate, pentasodium methane tetraphosponate, hexasodium methane tetraphosphonate, heptasodium methane tetraphosphonate, octasodium methane tetraphosphonate, mono potassium methane tetraphosphonate, tetra potassium methane tetraphosphonate, octa potassium methan tetraphosphonate, mono ammonium methane tetraphosphonate, octa ammonium methane tetraphosphonate, monosodium methane triphosphonate, trisodium methane triphosphonate, pentasodium methane triphosphonate, hexasodium methane triphosphonate, di potassium methane triphosphate, tetra potassium methane triphosphonate, hexa potassium methane triphosphonate, mono ammonium methane triphosphonate, hexa ammonium methane triphosphonate, monosodium chloromethane triphosphonate, tetrasodium chloromethane triphosphonate, hexasodium chloromethane triphosphonate, mono potassium chloromethane triphosphonate, tri ammonium chloromethane triphosphonate, hexa ammonium choromethane triphosphonate, monosodium chloromethane diphosphonate, disodium chloromethane diphosphonate, trisodium chloromethane diphosphonate, tetrasodium chloromethane diphosphonate, mono potassium chlormethane diphosphonate, tetra potassium chloromethane diphosphonate, di ammonium chloromethane diphosphonate, tetra ammonium chloromethane diphosphonate, monosodium dichloromethane diphosphonate, disodium dichloromethane diphosphonate, tetrasodium dichloromethane diphosphonate, tri potassium dichloromethane diphosphonate, tetra potassium dichloromethane diphosphonate, mono ammonium dichloromethane diphosphonate, tetra ammonium dichloromethane diphosphonate, monosodium phenyl methane triphosphonate, trisodium phenyl methane triphosphonate, hexasodium phenyl methane triphosphonate, tetra potassium phenyl methane triphosphonate, hexa potassium phenyl methane triphosphonate, hexa ammonium phenyl methane triphosphonate, tetrasodium hydroxymethane diphosphonate, monosodium methyl hydroxymethane diphosphonate, disodium methyl hydroxymethane diphosphonate, trisodium methyl hydroxymethane diphosphonate, tetrasodium methyl hydroxymethane diphosphonate, potassium methyl hydroxymethane diphosphonate, tetra potassium methyl hydroxymethane diphosphonate, di ammonium methyl hydroxymethane diphosphonate, tetra ammonium methyl hydroxymethane diphosphonate, monosodium ethyl hydroxymethane diphosphonate, tetrasodium ethyl hydroxymethane diphoshoate, tri potassium ethyl hydroxymethane diphosphonate, tetra ammonium ethyl hydroxymethane diphosphonate, monosodium propyl hydroxymethane diphosphonate, tetrasodium propyl hydroxymethane diphosphonate, dipotassium propyl hydroxymethane diphosphonate, tri ammonium propyl hydroxymethane diphosphonate, disodium isopropyl hydroxymethane diphosphonate, tetra potassium isopropyl hydroxymethane diphosphonate, monosodium chloromethyl hydroxymethane diphosphonate, tetrasodium dichloromethyl hydroxymethane diphosphonate, tetrasodium chloromethyl hydroxymethane diphosphonate, mono potassium chloromethyl hydroxymethane diphosphonate, di potassium chloromethyl hydroxymethane diphosphonate, tetra ammonium chloromethyl hydroxymethane diphosphonate, mono potassium dichloromethyl hydroxymethane diphosphate, monosodium trichloromethyl hydroxymethane diphosphonate, disodium trichloromethyl hydroxymethane diphosphonate, tetrasodium trichloromethyl hydroxymethane diphosphonate, mono potassium trichloromethyl hydroxymethane diphosphonate, tetra potassium trichloromethyl hydroxymethane diphosphonate, diammonium trichloromethyl hydroxymethane diphosphonate, tetrasodium butyl hydroxymethane diphosphonate, tri potassium butyl hydroxymethane diphosphonate, mono ammonium butyl hydroxymethane diphosphonate, monosodium pentyl hydroxymethane diphosphonate, tetrasodium pentyl hydroxymethane phosphate, di potassium pentyl hydroxymethane diphosphonate, monosodium hexyl hydroxymethane diphosphonate, trisodium hexyl hydroxymethane diphosphonate, tetrasodium hexyl hydroxymethane diphosphonate, tetra potassium hexyl hydroxymethane disphosphonate, tetra ammonium hexyl hydroxymethane diphosphonate, tetrasodium heptyl hydroxymethane diphosphonate, disodium heptyl hydroxymethane diphosphonate, mono potassium heptyl hydroxymethane diphosphonate, tri ammonium heptyl hydroxymethane diphosphonate, monosodium octyl hydroxymethane diphosphonate, trisodium octyl hydroxymethane diphosphate, tetrasodium octyl hydroxymethane diphosphonate, tetra potassium octyl hydroxymethane diphosphonate, tetrasodium nonyl hydroxymethane diphosphonate, tetra ammonium octyl hydroxymethane diphosphonate, tetra potassium nonyl hydroxymethane diphosphonate, tetra ammonium nonyl hydroxymethane diphosphonate, disodium nonyl hydroxymethane diphosphate, tetrasodium decyl hydroxymethane diphosphonate, di potassium decyl hydroxymethane diphosphonate, mono ammonium decyl hydroxymethane diphosphonate, monosodium isononyl hydroxymethane diphosphonate, tetrasodium isononyl hydroxymethane diphosphonate, trisodium undecyl hydroxymethane diphosphonate, tetra potassium undecyl hydroxymethane diphosphonate, tetrasodium undecyl hydroxymethane diphosphonate, tetra ammonium undecyl hydroxymethane diphosphonate, tetrasodium dodecyl hydroxymethane diphosphonate, tetrasodium tridecyl hydroxymethane diphosphonate, tetra potassium tetradecyl hydroxymethane diphosphonate, monosodium pentadecyl hydroxymethane diphosphonate, trisodium pentadecyl hydroxymethane diphosphonate, tetrasodium pentadecyl hydroxymethane diphosphonate, di potassium pentadecyl hydroxymethane diphosphonate, tetra ammonium pentadecyl hydroxymethane diphosphonate, tetrasodium hexadecyl hydroxymethane diphosphonate, monosodium heptadecyl hydroxymethane diphosphonate, disodium heptadecyl hydroxymethane diphosphonate, trisodium heptadecyl hydroxymethane diphosphonate, tetrasodium heptadecyl hydroxymethane diphosphonate, mono potassium heptadecyl hydroxymethane diphosphonate, tetra potassium heptadecyl hydroxymethane diphosphonate, mono ammonium heptadecyl hydroxymethane diphosphonate, tetrasodium octadecyl hydroxymethane methane diphosphonate, tetrasodium nonadecyl hydroxymethane diphosphonate, tetra potassium nonadecyl hydroxymethane diphosphonate, tetra ammonium nonadecyl hydroxymethane diphosphonate, tetrasodium vinyl hydroxymethane diphosphonate, tetra potassium isopropenyl hydroxymethane diphosphonate, monosodium heptadecenyl hydroxymethane diphosphonate, disodium heptadecenyl hydroxymethane diphosphonate, trisodium heptadecenyl hydroxymethane diphosphonate, tetrasodium heptadecenyl hydroxymethane diphosphonate, mono potassium heptadecenyl hydroxymethane diphosphonate, tetra potassium heptadecenyl hydroxymethane diphosphonate, di ammonium heptadecenyl hydroxymethane diphosphonate, tetra ammonium heptadecenyl hydroxymethane diphosphonate, tetrasodium naphthyl hydroxymethane diphosphonate, monosodium phenyl hydroxymethane diphosphonate, disodium phenyl hydroxymethane diphosphonate, trisodium phenyl hydroxymethane diphosphonate, tetrasodium phenyl hydroxymethane diphosphonate, di potassium phenyl hydroxymethane diphosphonate, tetra potassium phenyl hydroxymethane diphosphonate, tetra ammonium phenyl hydroxymethane diphosphonate, monosodium phenyl methane diphosphonate, disodium phenyl methane diphosphonate, trisodium phenyl methane diphosphonate, tetrasodium phenyl methane diphosphonate, tetra potassium phenyl methane diphosphonate, tetra ammonium phenyl methane diphosphonate, tetrasodium p-chlorophenyl hydroxymethane diphosphonate, tetrasodium 2, 4, 5-trichlorophenyl hydroxymethane diphosphonate, tetra potassium 2, 4, 6-trichlorophenyl hydroxymethane diphosphonate.

Some of the polyphosphonic acids and salts employed in the present invention are old as shown for example, in Blaser U.S. Pat. No. 3,122,417 and Schiefer U.S. Pat. No. 3,149,151. In general the acids and salts can be prepared by the methods shown in Schiefer. Many of the free acids can also be formed by hydrolyzing the corresponding esters such as the esters shown in Schmidt U.S. Pat. No. 2,848,475, for example. Preferably a lower alkyl ester is employed for such a hydrolysis and aqueous hydrochloric acid is used as the hydrolyzing agent as is illustrated infra. In such case the alkali metal or ammonium salts are formed by dissolving the free acid in aqueous sodium hydroxide or potassium hydroxide or ammonium hydroxide and evaporating to dryness, e.g. by spray drying. Sufficient alkali is employed to neutralize from one up to all the acid groups available on the phosphonic acid. The free methane triphosphonic acid, methane tetraphosphonic acid, chloromethane triphosphonic acid, chloromethane diphosphonic acid and dichloromethane diphosphonic acid and their salts can be prepared in the manner set forth in the U.S. Pat. No. 3,471,552.

The methane triphosphonic acid, methane tetraphosphonic acid. chloromethane triphosphonic acid and phenyl methane triphosphonic acid and their alkali metal salts are better phosphonic acid builders in the detergent compositions than methane diphosphonic acid and its alkali metal salts and also sequester more calcium and magnesium ions, for example than does methane diphosphonic acid or its alkali metal salts. The alkali metal salts also are more nearly neutral since the tri and tetra phosphonic acids are stronger acids than methane diphosphonic acid.

The hydroxy containing methane diphosphonic acids and alkali metal salts of the present invention, e.g., methyl hydroxymethane diphosphonic acid and phenyl hydroxymethane diphosphonic acid and their alkali metal salts, have better solubility than the corresponding methane diphosphonic acid or its salts. Additionally the hydroxy containing compounds have better stability and complex formation properties due to hydrogen bonding available through the hydroxyl hydrogen. The chlorine containing polyphosphonic acids (and salts) used in the present invention have improved sebum stain removing properties than the corresponding methane diphosphonic acid (and salts).

The alkyl and alkenyl methane diphosphonic acids (and salts) having at least 8 atoms in the alkyl or alkenyl group have surface activity and lower surface tension properties in their own right which are not exhibited by methane diphosphonic acid or lower alkyl or alkenyl methane diphosphonic acids (or their salts). Preferably the alkyl group has at least 10 carbon atoms, must preferably at least 12 carbon atoms.

The aryl methane diphosphonic acids (and salts) also exhibit these lower surface tension and surface activity properties. The aryl containing compounds, e.g., phenyl methane diphosphonic acid, phenyl hydroxymethane diphosphonic acid and phenyl methane triphosphonic acid (and their salts) are superior for metal extraction, e.g., extraction of gold, silver, vanadium, molybdenum, copper, nickel and iron.

All of the polyphosphonic acids (and salts) of the present invention are valuable in prevention of the reversion of polyphosphates, e.g., sodium tripolyphosphate, and pyrophosphates, e.g., tetra potassium pyrophosphate.

Unless otherwise indicated all parts and percentages are by weight.

The detergent compositions of the present invention normally contain 5–90% of detergent, usually 10–50%; and 10–80% of builder, usually 20–60%. The builder can be from 0.5–100% of the polyphosphonates (substituted methane) of the present invention with the balance being conventional phosphates, polyphosphates and pyrophosphates. If desired some methane diphosphonic acid or its alkali metal salts can be included.

Silicates can be used as corrosion inhibitors in an amount of 1–30%, usually 2–10% of the composition or they can be omitted. Borax can be added as a water softener in an amount of 1–40% or it can be omitted.

The detergents can be anionic, cationic, or nonionic. Preferably they are anionic.

Examples of suitable detergents are sodium stearate (soap), sodium palmitate, sodium elaidate, potassium stearate, potassium oleate, sodium oleate, higher alkylaryl sulfonates containing 8–22 carbon atoms in the alkyl group, e.g., higher alkyl benzene sulfonates, higher alkyl toluene sulfonates and higher alkyl phenol sulfonates. Thus there can be used sodium decylbenzene sulfonate, sodium dodecyl benzene sulfonate, potassium dodecyl benzene sulfonate, sodium keryl sulfonate, sodium nonyl benzene sulfonate, sodium decylphenol sulfonate, potassium pentadecyl benzene sulfonate, ammonium dodecyl benzene sulfonate, triethanolamine decyl benzene sulfonate, monoethanolamine dodecyl toluene sulfonate, sodium octadecyl benzene sulfonate, diethanolamine tetradecyl benzene sulfonate. Normally the alkali metal salts, e.g., the sodium or potassium salts, of the higher alkyl aromatic sulfonic acids are used but as indicated ammonium or amine salts are used. The alkyl groups can be branched or straight chain depending upon the method of manufacturing the higher alkyl aromatic sulfonic acid as is well known in the art.

Other anionic detergents include normally and secondary higher alkyl sulfate detergents, particularly the alkali metal salts of such sulfates, those having 8 to 22 carbon atoms in the alkyl residue such as sodium lauryl sulfate, potassium lauryl sulfate, sodium octadecyl sulfate, sodium coconut fatty alcohol sulfate, sodium octanyl sulfate, sodium alkyl ($C_{14}$–$C_{18}$) sulfate, as well as the corresponding long chain aliphatic sulfonates, e.g., sodium octanyl sulfonate, sodium dodecyl sulfonate, sodium tetradecyl sulfonate, sodium octadecyl sulfonate, potassium dodecyl sulfonate, ammonium dodecyl sulfonate, sodium decyl sulfonate, higher alkyl ether sulfates, higher alkyl glyceryl ether sulfonates, higher alkyl phenol polyethylene oxide sulfates, polyoxyethyl ethers of fatty alcohols, polyethylene oxide condensates with higher alkyl phenols such as isooctyl and nonyl phenol condensed with 8 to 20 moles of ethylene oxide, preferably about 10, and polyethylene condensates with hydrophobic polypropylene glycols e.g., pluronic L-64, sodium o-xylene sulfonate, potassium xylene sulfonate, potassium tertiary octylbenzene sulfonate, potassium dodecyl toluene sulfonate, sodium p-xylylene sulfonate, sodium propyl naphthalene sulfonate, sodium butyl-naphthalene sulfonate.

Suds builders can be added such as alkylolamides, e.g., alkyl ($C_8$–$C_{18}$) monoethanolamide, higher fatty alcohols, e.g. stearyl alcohol and oleyl alcohol, cationic detergents such as lauramidodipropyl dimethyl benzyl ammonium chloride and N-diethyl amino oleylamide hydrochloride.

As indicated any of the conventional phosphate builders can be included and the polyphosphonates of the present invention reduce the tendency of the polyphosphates toward reversion. Examples of phosphate builders are sodium hexametaphosphate, sodium tripolyphosphate, tetrasodium pyrophosphate, trisodium phosphate, tetrapotassium pyrophosphate, potassium tripolyphosphate, sodium tripolyphosphate, pentapotassium tripolyphosphate.

Any of the conventional alkali metal silicate builders can also be employed in addition to or in place of the polyphosphates. Typical examples of suitable silicates have an alkali oxide to silica ratio within the range of from 1:1 to 1:4 are preferably from about 1:2 to 1:3. Examples are sodium silicates having an $Na_2O$ to $SiO_2$ mole ratio of 1:2.35; 1:2.5, 1:3.2, 1:2.0; 1:1.6 and 1:1.

Borax and sodium carbonate can also be present and normally there is also present some sodium sulfate or potassium sulfate in the detergent.

Brighteners and other conventional additives to detergent composition can also be present. Thus there can be used polyvinyl alcohol (PVA) and carboxymethylcellulose (CMC).

EXAMPLE 1

166.2 grams (1 mole) triethyl phosphate was added dropwise with stirring to 78.4 grams (1 mole) of acetyl chloride over a period of 30 minutes at a temperature of 30° to 35° C. maintained by cooling. Ethyl chloride was evolved. The temperature was increased to 60° C. over the next 1 hour and 15 minutes, at which time the evolution of ethyl chloride was complete. The product was distilled under vacuum yeilding 176 grams of diethyl acetylphosphonate (DEAP) in 98% yield, B.P. about 80° C. at 5 mm. and having a refractive index of 1.4240 at 200° C.

Then to 11.83 grams (0.9 mole) of diethyl phosphite there were added 2.4 grams of sodium metal. The reaction was exothermic at about 60° C. when all the sodium had reacted. Then the DEAP was added dropwise over a 15 minute period at 60° to 90° C. Heating was continued and the temperature held at 100° C. for an additional hour. The product was then distilled to give tetraethyl methyl hydroxymethane diphosphonate (also called tetraethyl 1-hydroxyethylidene diphosphonate) in a yield of 286 grams (90%) B.P. 150° to 160° C. at 1.5 mm 0.9 mole of tetraethyl 1-hydroxyethylidene diphosphonate was refluxed with 5.4 moles of concentrated hydrochloric acid for 12 hours. Excess acid was removed by stripping under vacuum. 200 ml. of water were added and removed in vacuo, then finally, 200 ml. of benzene were added and the water removed and separated by means of a Dean and Starke trap and the benzene was distilled over under reduced pressure, yielding 184 grams (100% yield) of methyl hydroxymethane diphosphonic acid as a syrup having a neutralization equivalent of 1080 mg. KOH/gm. (Theory is 1087 mg. KOH/gm.); % P 3.05 (Theory 3.01%); % C 11.54 (Theory 11.65%); % H 2.90 (Theory 2.94%).

EXAMPLE 2

To 140.57 grams (1.0 mole) of benzoyl chloride at 90° C. there were added 166.2 grams (1.0 mole) of triethyl phosphite over a period of 1 hour. Ethyl chloride evolution ceased at the end of this period. The unreacted benzoyl chloride and triethyl phosphite were removed by distillation at reduced pressure, terminal conditions being 100° C. and 8 mm. leaving a residue of 236 grams (90% yield) of diethyl benzoylphosphonate which was reacted with diethyl sodium phosphite as in Example 1 to produce tetraethyl phenyl hydroxymethane diphosphonate. This was hydrolyzed and the hydrolysis product purified in the same manner as in Example 1 to produce phenyl hydroxymethane diphosphonic acid as a viscous syrup having an acid number of 822 mg. KOH/mg (Theory is 836 mg. KOH/gm); % P 22.8 (Theory 22.9%).

EXAMPLE 3

There were charged into the reaction vessel 23.0 grams (1.0 mole) of sodium metal along with 90 cc. of xylene and 80 cc. of tetrahydrofurane. The vessel was placed under a nitrogen blanket and 138.10 grams (1.0 mole) of diethyl phosphite added over a 35 minute period. An exothermic reaction ensued which was maintained at 62° C. by external cooling. After addition was complete the mixture was heated to 100° C. and held there until all of the sodium metal was gone. The mixture was cooled to 60° to 70° C. and 80.50 grams (0.5

,ole) of benzal chloride were added gradually over a 25 minute period. An exothermic reaction ensued which was maintained at 60° to 70° C. by external cooling. The mixture was then heated for 4 hours at 70° to 75° C., cooled to 60° C. The liquid material was separated from the solid and the solid boiled 8 times with 100 cc. of benzene to extract the organic material. The eluate product was then distilled, terminal conditions being a pot temperature of 201° C., distillate temperature 125° C. and pressure 6 mm. The solid residue of 70 grams was tetraethyl phenyl methane diphosphonate. This product was hydrolyzed and the hydrolysis product purifid as in Example 1 to obtain phenyl methane diphosphonic acid.

EXAMPLE 4

There were mixed together 23.0 grams (1.0 mole) of sodium metal along with 90 cc. of xylene and 80 cc. of tetrahydrofurane and the mixture placed under a nitrogen atmosphere. There were then added over a 35 minute period 138.10 grams (1.0 mole) of diethyl phosphite using external cooling to control the reaction exotherm and maintain the temperature at 60° to 65° C. After addition was complete the mixture was heated to 100° C. and maintained there for about 1 hour until there was no more sodium. The mixture was cooled to 60° C. and there was started the addition of 64.5 grams (0.33 mole) of benzotrichloride (α,α,α-trichlorotoluene). The exothermic reaction was cooled to maintain the temperature at 60° to 65° C. during the 25 minute addition period. The mixture was heated at 70° to 75° C. for 7 hours and the sodium chloride filtered off. The product in the pot was then subjected to distillation, terminal conditions being a pot temperature of 205° C., distillate temperature 125° C. and pressure 4 mm. The solid residue in the pot was hexaethyl phenyl methane triphosphonate. This product was hydrolyzed and the hydrolysis product purified as in Example 1 to obtain phenyl methane triphosphonic acid.

EXAMPLE 5

The procedure of Example 1 was repeated replacing the acetyl chloride by equal molar amounts of (a) propionyl chloride, (b) butyryl chloride, (c) isobutyryl chloride, (d) pentanoyl chloride, (e) caproyl chloride, (f) heptanoyl chloride, (g) octanoyl chloride, (h) nonanoyl chloride, (i) isodecanoyl chloride, (j) decanoyl chloride, (k) undecanoyl chloride, (l) dodecanoyl chloride, (m) tridecanoyl chloride, (n) hexadecanoyl chloride, (o) octadecanoyl chloride, (p) octadecenoyl chloride, (q) naphthanoyl chloride, (r) chloroacetyl chloride, (s) dichloroacetyl chloride, and (t) trichloroacetyl chloride to produce as the resultant hydrolysis products (a) ethyl hydroxymethane diphosphonic acid, (b) propyl hydroxymethane diphosphonic acid, (c) isopropyl hydroxymethane diphosphonic acid, (d) butyl hydroxymethane diphosphonic acid, (e) pentyl hydroxymethane diphosphonic acid, (f) hexyl hydroxymethane diphosphonic acid, (g) heptyl hydroxymethane diphosphonic acid, (h) octyl hydroxymethane diphosphonic acid, (i) isononyl hydroxymethane diphosphonic acid, (j) nonyl hydroxymethane diphosphonic acid, (k) decyl hydroxymethane diphosphonic acid, (l) undecyl hydroxymethane diphosphonic acid, (m) dodecyl hydroxymethane diphosphonic acid, (n) pentadecyl hydroxymethane diphosphonic acid, (o) heptadecyl hydroxymethane diphosphonic acid, (p) heptadecenyl hydroxymethane diphosphonic acid, (q) naphthyl hydroxymethane diphosphonic acid, (r) chloromethyl hydroxymethane diphosphonic acid, (s) dichloromethyl hydroxymethane diphosphonic acid and (t) trichloromethyl hydroxymethane diphosphonic acid.

EXAMPLE 6

To 1 mole of methyl hydroxymethane diphosphonic acid there were added 4 moles of 10% aqueous sodium hydroxide and the mixture was evaporated to dryness to produce tetrasodium methyl hydroxymethane diphosphonate.

EXAMPLE 7

To 1 mole of phenyl hydroxymethane diphosphonic acid there were added 4 moles of 10% aqueous sodium hydroxide and the mixture was evaporated to dryness to produce tetrasodium phenyl hydroxymethane diphosphonate.

EXAMPLE 8

To 1 mole of phenyl methane diphosphonic acid there were added 4 moles of 10% aqueous sodium hydroxide and the mixture was evaporated to dryness to produce tetrasodium phenyl methane diphosphonate.

EXAMPLE 9

To 1 mole of phenyl methane triphosphonic acid there were added 6 moles of 10% aqueous sodium hydroxide and the mixture was evaporated to dryness to produce hexasodium phenyl methane triphosphonate.

EXAMPLE 10

The procedure of Example 6 was repeated replacing the methyl hydroxymethane diphosphonic acid by each of the diphosphonic acids prepared in Example 5 (a) through (t) to produce respectively, (a) tetrasodium ethyl hydroxymethane diphosphonate, (b) tetrasodium propyl hydroxymethane diphosphonate, (c) tetrasodium isopropyl hydroxymethane diphosphonate, (d) tetrasodium butyl hydroxymethane diphosphonate, (e) tetrasodium pentyl hydroxymethane diphosphonate, (f) tetrasodium hexyl hydroxymethane diphosphonate, (g) tetrasodium heptyl hydroxymethane diphosphonate, (h) tetrasodium octyl hydroxymethane diphosphonate, (i) tetrasodium isononyl hydroxymethane diphosphonate, (j) tetrasodium nonyl hydroxymethane diphosphonate, (k) tetrasodium decyl hydroxymethane diphosphonate, (l) tetrasodium undecyl hydroxymethane diphosphonate, (m) tetrasodium dodecyl hydroxymethane diphosphonate, (n) tetrasodium pentadecyl hydroxymethane diphosphonate, (o) tetrasodium heptadecyl hydroxymethane diphosphonate, (p) tetrasodium heptadecenyl hydroxymethane diphosphonat, (q) tetrasodium naphthyl hydroxymethane diphosphonate, (r) tetrasodium chloromethyl hydroxymethane diphosphonate, (s) tetrasodium dichloromethyl hydroxymethane diphosphonate, (t) tetrasodium trichloromethyl hydroxymethane diphosphonate. The corresponding potassium and ammonium salts can be prepared by replacing the 10% sodium hydroxide by an equal molar amount of 10% potassium hydroxide or ammonium hydroxide.

The following examples illustrate various detergent formulations.

Ultrawet H is potassium xylene sulfonate.

EXAMPLE 11

The addition of 1% methyl hydroxymethane diphosphonic acid to sodium tripolyphosphate reduced its reversion to phosphate from 11% to 3% in boiling water over a 3 minute period. Similar results were obtained using 1% of tetrasodium methyl hydroxymethane diphosphonate. In place of the methyl hydroxymethane diphosphonic acid there can also be used in this example the same amount of (a) octyl hydroxymethane diphosphonic acid, (b) tetrasodium octyl hydroxymethane diphosphonic acid, (c) methane triphosphonic acid, (d) hexasodium methane triphosphonate, (e) methane tetraphosphonic acid, (f) octapotassium methane tetraphosphonate, (g) chloromethane triphosphonic acid, (h) disodium dichloromethane diphosphonate, (i) phenylhydroxymethane diphosphonic acid, (j) tetrasodium phenyl hydroxymethane diphosphonate, and (k) phenyl methane diphosphonic acid.

EXAMPLE 12

Octyl hydroxymethane diphosphonic acid, decyl hydroxymethane diphosphonic acid and their tetrasodium salts each reduced the surface tension of water from 70 dynes/cm. to less than 30 dynes/cm. when used at a concentration of 0.5%.

EXAMPLE 13

A detergency test with 0.10% Ultrawet K and increasing amounts of methyl hydroxymethane diphosphonic acid at pH 9.5 in water showed that methyl hydroxymethane diphosphonic acid was superior to phytic acid and sodium tripolyphosphate at every concentration tested, namely, from 0.05% to 0.30%. This superiority was also noted for methane triphosphonic acid, methane tetraphosphonic acid and chloromethane triphosphonic acid when used in the same conditions.

EXAMPLE 14

A solution of 0.002% of methyl hydroxymethane diphosphonic acid in a 0.05% aqueous solution of sodium metasilicate at a temperature of 90° C. protected the surface of aluminum immersed in it for at least 20 hours, while a control solution of the same sodium metasilicate caused extensive corrosion under the same conditions. Similarly, white metal, German silver, stainless steel and red brass were protected. In place of the methyl hydroxymethane diphosphonic acid there was also employed successfully the same amount of methane triphosphonic acid, methane tetraphosphonic acid, chloromethane triphosphonic acid and phenyl hydroxymethane diphosphonic acid.

EXAMPLE 15

"Fab" is a commercial detergent comprising Alfol 14–18 (a mixture of 14–18 carbon atom alkyl alcohols), LAS (linear alkane sulfonates containing 10–18 carbon atoms), KXS (potassium xylene sulfonate) and TKPP (tetrapotassium pyrophosphate). To improve the detergency power of "Fab" there was added 10% of methyl hydroxymethane diphosphonic acid.

The detergency power of "Fab" was also improved by adding 10% of each of the following materials (a) tetrasodium methyl hydroxymethane diphosphonate, (b) trisodium methyl hydroxymethane diphosphonate, (c) trisodium phenyl hydroxymethane diphosphonate, (d) tetrasodium phenyl hydroxymethane diphosphonate, (e) octasodium methane tetraphosphonate, (f) hexapotassium methane triphosphonate, (g) tetrasodium chloromethane diphosphonate, (h) tetrasodium decyl hydroxymethane diphosphonate or (i) disodium octadecenyl hydroxymethane diphosphonate.

EXAMPLE 16

| | | |
|---|---|---|
| Sodium dodecylbenzene sulfonate | 30 | parts |
| Sodium tripolyphosphate | 25 | parts |
| Sodium sulfate | 14 | parts |
| Sodium silicate | 5 | parts |
| Tetrasodium methyl hydroxymethane diphosphonate | 25 | parts |

This mixture can be dissolved in water to give a 0.2% detergent solution.

In place of the diphosphonate in Example 16 there can be used an equivalent amount of (a) octasodium methane tetraphosphonate, (b) tetrasodium methane tetraphosphonate, (c) hexasodium methane triphosphonate, (d) hexapotassium chloromethane triphosphonate, (e) tetrasodium trichloromethyl hydroxymethane diphosphonate, (f) tetrapotassium heptadecyl hydroxymethane diphosphonate, (g) tetrasodium phenyl hydroxymethane diphosphonate, or (h) tetrasodium ethyl hydroxymethane diphosphonate.

EXAMPLE 17

| | | |
|---|---|---|
| Sodium tridecyl benzene sulfonate | 30 | parts |
| Octasodium methane tetraphosphonate | 50 | parts |

This mixture can be dissolved in water to give a 0.2% detergent solution. In place of the tetraphosphonate there can be used an equal amount of (a) tetrasodium methyl hydroxymethane diphosphonate, (b) trisodium methyl hydroxymethane diphosphonate, (c) hexasodium methane triphosphonate, (d) tetrasodium dichloromethane diphosphonate, (e) pentasodium phenyl methane triphosphonate, (f) tetrasodium phenyl hydroxymethane diphosphonate, (g) tetrasodium chloromethyl hydroxymethane diphosphonate.

EXAMPLE 18

| | | |
|---|---|---|
| Sodium stearate | 60 | parts |
| Soda ash | 15 | parts |
| Tetrasodium pyrophosphate | 5 | parts |
| Methane tetraphosphonic acid | 10 | parts |

This mixture also was a good detergent at 0.2% concentration. Soil redeposition properties of the composition were enhanced by adding 5 parts of polyvinyl alcohol and 5 parts of carboxymethyl cellulose. In place of the methane tetraphosphonic acid in Example 18 there can be used an equal amount of (a) octasodium methane tetraphosphonate, (b) methane triphosphonic acid, (c) hexasodium methane triphosphonate, (d) tetrasodium methyl hydroxymethane diphosphonate, (e) tetrasodium phenyl hydroxymethane diphosphonate, or (f) tetrasodium isononyl hydroxymethane diphosphonate.

EXAMPLE 19

| | | |
|---|---|---|
| Sodium hexadecane sulfonate | 15 | parts |
| Sodium tripolyphosphate | 5 | parts |
| Tetrasodium methyl hydroxymethane diphosphonate | 5 | parts |
| Soda ash | 5 | parts |

EXAMPLE 20

| | |
|---|---|
| Sodium tridecyl benzene sulfonate | 40 parts |
| Sodium tripolyphosphate | 15 parts |
| Trisodium phenyl hydroxymethane diphosphonate | 20 parts |
| Sodium silicate | 10 parts |
| Sodium sulfate | 15 parts |
| Sodium carboxymethyl cellulose | 0.3 part |
| Polyvinyl alcohol (viscosity 2.34 centipoises, 22.3% polyvinyl acetate) | 0.3 parts |

EXAMPLE 21

| | |
|---|---|
| Sodium tridecyl benzene sulfonate | 17 parts |
| Cocoanut monoethanolamide | 3 parts |
| Sodium tripolyphosphate | 15 parts |
| Hexasodium methane triphosphonate | 30 parts |
| Sodium toluene sulfonate | 2.4 parts |
| Sodium silicate | 5.5 parts |
| Sodium sulfate | 18 parts |

EXAMPLE 22

| | |
|---|---|
| Nonylphenol-ethylene oxide adduct (9.5 ethylene oxide units) | 12 parts |
| Sodium tridecyl benzene sulfonate | 1.75 parts |
| Sodium tripolyphosphate | 20 parts |
| Hexasodium chloromethane triphosphate | 20 parts |
| Sodium sulfate | 35 parts |
| Fluorescent dye | 0.2 part |

The sodium tridecyl benzene sulfonate had an alkyl group derived from a mixture of propylene tetramer and pentamer and averaged to a tridecyl group.

In place of the triphosphonate there can be used in this example the same amount of (a) tetrasodium propyl hydroxymethane diphosphonate, (b) octasodium methane tetraphosphonate, (c) tetrasodium decyl hydroxymethane diphosphonate, or (d) tetrasodium trichloromethyl diphosphonate.

EXAMPLE 23

| | |
|---|---|
| Sodium tridceyl benzene sulfonate | 8 parts |
| Nonylphenol-ethylene oxide adduct | 6 parts |
| Sodium tripolyphosphates | 15 parts |
| Tetrasodium methane triphosphonate | 20 parts |
| Cetyl alcohol | 0.8 part |
| Sodium silicate | 3.0 parts |
| Sodium sulfate | 37.8 parts |
| Sodium carboxymethyl cellulose | 0.3 part |
| Polyvinyl alcohol | 0.13 part |

EXAMPLE 24

| | |
|---|---|
| Sodium hardened tallow alcohol sulfate | 10 parts |
| Pentasodium tripolyphosphate | 15 parts |
| Tetrasodium ethyl hydroxymethane diphosphonate | 20 parts |
| Sodium silicate | 10 parts |
| Sodium carbonate | 15 parts |
| Sodium carboxymethyl hydroxymethyl cellulose | 0.5 part |
| Sodium sulfate | 19.45 parts |

The compounds of formulae I, II and III supra are also useful in chelating compositions.

Examples of phosphonic acids and their salts useful in the chelating compositions of the present invention are chloromethane diphosphonic acid, dichloromethane diphosphonic acid, bromomethane diphosphonic acid, dibromomethane diphosphonic acid, chloromethane triphosphonic acid, bromomethane triphosphonic acid, methane triphosphonic acid, methane tetraphosphonic acid, hydroxymethane diphosphonic acid, methyl hydroxymethane diphosphonic acid (also called methyl hydroxymethylene diphosphonic acid or 1-methyl-1-hydroxymethane diphosphonic acid), ethyl hydroxymethane diphosphonic acid, butyl hydroxymethane diphosphonic acid, propyl hydroxymethane diphosphonic acid, isopropyl hydroxymethane diphosphonic acid, pentyl hydroxymethane diphosphonic acid, hexyl hydroxymethane diphosphonic acid, heptyl hydroxymethane diphosphonic acid, isoheptyl hydroxymethane diphosphonic acid, octyl hydroxymethane diphosphonic acid, nonyl hydroxymethane diphosphonic acid, decyl hydroxymethane diphosphonic acid, undecyl hydroxymethane diphosphonic acid, dodecyl hydroxymethane diphosphonic acid, tridecyl hydroxymethane diphosphonic acid, pentadecyl hydroxymethane diphosphonic acid, heptadecyl hydroxymethane diphosphonic acid, octadecyl hydroxymethane diphosphonic acid, nonadecyl hydroxymethane diphosphonic acid, heptadecenyl hydroxymethane diphosphonic acid, vinyl hydroxymethane diphosphonic acid, isopropenyl hydroxymethane diphosphonic acid, chloromethyl hydroxymethane diphosphonic acid, dichloromethyl hydroxymethane diphosphonic acid, trichloromethyl hydroxymethane diphosphonic acid, phenyl hydroxymethane diphosphonic acid, phenyl methane diphosphonic acid, phenyl methane triphosphonic acid, naphthyl hydroxy methane diphosphonic acid, p-chlorophenyl hydroxy methane diphosphonic acid, 2,4,5-trichlorophenyl hydroxy methane diphosphonic acid, 2,4,6-trichlorophenyl hydroxy methane diphosphonic acid, isononyl hydroxy methane diphosphonic acid and the alkali metal and ammonium salts of such phosphonic acids.

Since the phosphonic acids used in the present invention have 4, 6, or 8 acidic hydrogen atoms (Formulae I, II and III respectively) in making the salts one or more of the acidic hydrogen atoms can be replaced by the alkali metal or ammonium ion. Usually all of the acidic hydrogen atoms are replaced in making the salt and unless otherwise indicated when reference is made to a salt in the present specification, all of the acidic hydrogen atoms are replaced. However, it should be understood that this is not an essential part of the present invention and the invention includes the use of the partial as well as the complete salts, e.g., monosodium methane tetraphosphonate, disodium methane tetraphosphonate, trisodium methane tetraphosphonate, tetrasodium methane tetraphosphonate, pentasodium methane tetraphosphonate, hexasodium methane tetraphosphonate, heptasodium methane tetraphosphonate, octasodium methane tetraphosphonate, mono potassium methane tetraphosphonate, tetra potassium methane tetraphosphonate, octa potassium methane tetraphosphonate, mono ammonium methane tetraphosphonate, octa ammonium methane tetraphosphonate, monosodium methane triphosphonate, trisodium methane triphosphonate, pentasodium methane triphosphonate, hexasodium methane triphosphonate, di potassium methane triphosphonate, tetra potassium methane triphosphonate, hexa potassium methane triphosphonate, mono ammonium methane triphosphonate, hexa ammonium methane triphosphonate, monosodium chloromethane triphosphonate, tetrasodium chloromethane triphosphonate, hexasodium chloromethane triphosphonate, monopotassium chloromethane triphosphonate, tri ammonium chloromethane triphosphonate, hexa ammonium chloromethane triphosphonate, monosodium chloromethane diphosphonate, disodium chloromethane diphosphonate, trisodium chloromethane diphosphonate, tetrasodium chloromethane diphosphonate, mono potassium chloromethane diphosphonate, tetra potassium chloromethane diphosphonate, di ammonium chloromethane diphosphonate, tetra ammonium chloromethane diphosphonate, monosodium dichloromethane diphosphonate, disodium dichloromethane diphosphonate, tetrasodium dichloromethane diphosphonate, tri potassium dichloromethane diphosphonate, tetra potassium dichloromethane diphosphonate, mono ammonium dichloromethane diphosphonate, tetra ammonium dichloromethane diphosphonate, monosodium phenyl methane triphosphonate, trisodium phenyl methane triphosphonate, hexasodium phenyl methane triphosphonate, tetra potassium phenyl methane triphosphonate, hexa potassium phenyl methane triphosphonate, hexa ammonium phenyl methane triphosphonate, tetrasodium hydroxymethane diphosphonate, monosodium methyl hydroxymethane diphosphonate, disodium methyl hydroxymethane diphosphonate, trisodium methyl hydroxymethane diphosphonate, tetrasodium methyl hydroxymethane diphosphonate, potassium methyl hydroxymethane diphosphonate, tetra potassium methyl hydroxymethane diphosphonate, diammonium methyl hydroxymethane diphosphonate, tetra ammonium methyl hydroxymethane diphosphonate, monosodium ethyl hydroxymethane diphosphonate, tetrasodium ethyl hydroxymethane diphosphonate, tri potassium ethyl hydroxymethane diphosphonate, tetra ammonium ethyl hydroxymethane diphosphonate, monosodium propyl hydroxymethane diphosphonate, tetrasodium propyl hydroxymethane diphosphonate, di potassium propyl hydroxymethane diphosphonate, tri ammonium propyl hydroxymethane diphosphonate, disodium isopropyl hydroxymethane diphosphonate, tetra potassium isopropyl hydroxymethane diphosphonate, monosodium chloromethyl hydroxymethane diphosphonate, tetrasodium dichloromethyl hydroxymethane diphosphonate, tetrasodium chloromethyl hydroxymethyl diphosphonate, di potassium chloromethyl hydroxymethane diphosphonate, tetra ammonium chloromethyl hydroxymethane diphosphonate, mono potassium dichloromethyl hydroxymethane diphosphonate, monosodium trichloromethyl hydroxymethane diphosphonate, disodium trichloromethyl hydroxymethane diphosphonate, tetrasodium trichloromethyl hydroxymethane diphosphonate, mono potassium trichloromethyl hydroxymethane diphosphonate, tetra potassium trichloromethyl hydroxymethane diphosphonate, diammonium trichloromethyl hydroxymethane diphosphonate, tetrasodium butyl hydroxymethane diphosphonate, tri potassium butyl hydroxymethane diphosphonate, mono ammonium butyl hydroxymethane diphosphonate, monosodium pentyl hydroxymethane diphosphonate, tetrasodium pentyl hydroxymethane diphosphonate, di potassium pentyl hydroxymethane diphosphonate, monosodium hexyl hydroxymethane diphosphonate, trisodium hexyl hydroxymethane diphosphonate, tetrasodium hexyl hydroxymethane diphosphonate, tetra potassium hexyl hydroxymethane diphosphonate, tetra ammonium hexyl hydroxymethane diphosphonate, tetrasodium heptyl hydroxymethane diphosphonate, disodium heptyl hydroxymethane diphosphonate, mono potassium heptyl hydroxymethane diphosphonate, tri ammonium heptyl hydroxymethane diphosphonate, monosodium octyl hydroxymethane diphosphonate, trisodium octyl hydroxymethane diphosphonate, tetrasodium octyl hydroxymethane diphosphonate, tetra potassium octyl hydroxymethane diphosphonate, tetrasodium nonyl hydroxymethane diphosphonate, tetra ammonium octyl hydroxymethane diphosphonate, tetra potassium nonyl hydroxymethane diphosphonate, tetra ammonium nonyl hydroxymethane diphosphonate, disodium nonyl hydroxymethane diphosphonate, tetrasodium decyl hydroxymethane diphosphonate, di potassium decyl hydroxymethane diphosphonate, mono ammonium decyl hydroxymethane diphosphonate, monosodium isononyl hydroxymethane diphosphonate, tetrasodium iononyl hydroxymethane diphosphonate, trisodium undecyl hydroxymethane diphosphonate, tetra potassium undecyl hydroxymethane diphosphonate, tetrasodium undecyl hydroxymethane diphosphonate, tetra ammonium undecyl hydroxymethane diphosphonate, tetrasodium dodecyl hydroxymethane diphosphonate, tetrasodium tridecyl hydroxymethane, diphosphonate, tetra potassium tetradecyl hydroxymethane diphosphonate, monosodium pentadecyl hydroxymethane diphosphonate, trisodium pentadecyl hydroxymethane diphosphonate, tetrasodium pentadecyl hydroxymethane diphosphonate, di potassium pentadecyl hydroxymethane diphosphonate, tetra ammonium pentadecyl hydroxymethane diphosphonate, tetrasodium hexadecyl hydroxymethane diphosphonate, monosodium heptadecyl hydroxymethane diphosphonate, disodium heptadecyl hydroxymethane diphosphonate, trisodium heptadecyl hydroxymethane diphosphonate, tetrasodium heptadecyl hydroxymethane diphosphonate, mono potassium heptadecyl hydroxymethane diphosphonate, tetra potassium heptadecyl hydroxymethane diphosphonate, mono ammonium heptadecyl hydroxymethane diphosphonate, tetrasodium octadecyl hydroxymethane diphosphonate, tetrasodium nonadecyl hydroxymethane diphosphonate, tetra potassium nonadecyl hydroxymethane diphosphonate, tetra ammonium nonadecyl hydroxymethane diphosphonate, tetrasodium vinyl hydroxymethane diphosphonate, tetra potassium isopropenyl hydroxymethane diphosphonate, monosodium heptadecenyl hydroxymethane diphosphonate, disodium heptadecenyl hydroxymethane diphosphonate, trisodium heptadecenyl hydroxyethane diphosphonate, tetrasodium heptadecenyl hydroxymethane diphosphonate, mono potassium heptadecenyl hydroxymethane diphosphonate, tetra potassium heptadecenyl hydroxymethane diphosphonate, di ammonium heptadecenyl hydroxymethane diphosphonate, tetra ammonium heptadecenyl hydroxymethane diphosphonate, tetrasodium naphthyl hydroxymethane diphosphonate, monosodium phenyl hydroxymethane diphosphonate, disodium phenyl hydroxymethane diphosphonate, trisodium phenyl hydroxymethane diphosphonate, tetrasodium phenyl hydroxymethane diphosphonate, di potassium phenyl hydroxymethane diphosphonate, tetra potassium phenyl hydroxymethane diphosphonate, tetra ammonium phenyl hydroxymethane diphosphonate, monosodium phenyl methane diphosphonic disodium phenyl methane diphosphonate, trisodium phenyl methane diphosphonate, tetrasodium phenyl methane diphosphonate, tetra potassium phenyl methane diphosphonate, tetra ammonium phenyl methane diphosphonate, tetrasodium p-chlorophenyl hydroxymethane diphosphonate, tetrasodium 2,4,5-trichlorophenyl hydroxymethane diphosphonate, tetra potassium 2,4,6-trichlorophenyl hydroxymethane diphosphonate.

Alkyltin and aryltin salts (e.g., mono, di or trialkytin salts) can also be made.

The methane triphosphonic acid, methane tetraphosphonic acid, chloromethane triphosphonic acid and phenyl methane triphosphonic acid and their alkali metal salts are better chelating agents than, for example, methane diphosphonic acid or its alkali metal salts. The alkali metal salts are also more nearly neutral since the tri and tetra phosphonic acids are stronger acids then methane diphosphonic acid.

The novel chelators disclosed herein are better chelating agents for metal ions such as ferric ions than, for example, the well-known conventional sequestering agent ethylene diamine tetraacetic acid.

The hydroxy containing methane diphosphonic acids and alkali metal salts of the present invention, e.g., methyl hydroxymethane diphosphonic acid and their alkali metal salts, have better solubility than the corresponding methane diphosphonic acid or its salts. Additionally, the hydroxy containing compounds have better stability and complex formation properties due to hydrogen bonding available through the hydroxyl hydrogen. All of the above properties of the hydroxy containing compounds are extremely important in processes, such as in the treatment of textile materials, where it is necessary to tie up the calcium and other metal ions in solution and to not to allow these ions to precipitate out so as to discolor the product being treated.

The aryl containing compounds, e.g., phenyl methane diphosphonic acid, phenyl hydroxymethane diphosphonic acid and phenyl methane triphoshonic acid (and their salts), etc., are superior chelating agents for metal extraction, e.g., extraction of gold, silver, vanadium, molybdenum, copper, nickel and iron.

The novel chelating agents disclosed herein are not effective sequesters of mono-valent alkali metals, e.g., lithium, sodium and potassium. They will effectively chelate, however, mono-valent heavy metals such as silver and gold. In general, the chelating agents of the present invention are excellent sequesters of metals belonging to groups Ib, IIa, IIb, IIIa, IIIb, IVa, IVb, Va, Vb, VIa, VIb, VIIa, and VIII in the periodic system of elements. Examples of metals belonging to these groups are copper, silver, gold, magnesium, calcium, barium, zinc, cadmium, mercury, germanium, tin, titanium, zirconium, radium, platinum, palladium, rare earth, e.g. hafnium and cerium, vanadium, chromium, molybdenum, tungsten, uranium, manganese, iron, cobalt and nickel, etc. Thus the novel chelating agents of the present invention are effective chelators of non-alkali metal ions.

Illustrative examples of chelated salts are calcium chloromethane diphosphonate, barium chloromethane diphosphonate, magnesium chloromethane diphosphonate, beryllium chloromethane diphosphonate, zinc chloromethane diphosphonate, cadmium chloromethane diphosphonate, mercury chloromethane diphosphonate, cupric chloromethane diphosphonate, silver chloromethane diphosphonate, auric chloromethane diphosphonate, titanium chloromethane diphosphonate, zirconium chloromethane diphosphonate, stannous chloromethane diphosphonate, stannic chloromethane diphosphonate, chromic chloromethane diphosphonate, tungsten chloromethane diphosphonate, molybdenum chloromethane diphosphonate, manganous chloromethane diphosphonate, ferrous chloromethane diphosphonate, ferric chloromethane diphosphonate, cobaltic chloromethane diphosphonate, nickelous chloromethane diphosphonate, platinum chloromethane diphosphonate, palladium chloromethane diphosphonate, uranium chloromethane, diphosphonate, uranyl chloromethane diphosphonate, plumbous chloromethane diphosphonate, hafnium chloromethane diphosphonate, cerium chloromethane diphosphonate, dibutyltin chloromethane diphosphonate, monobutyltin chloromethane diphosphonate, tributyltin chloromethane diphosphonate, dioctyltin chloromethane diphosphonate, diphenyltin chloromethane diphosphonate, calcium bromomethane diphosphonate, ferric bromomethane diphosphonate, barium dibromomethane diphosphonate, cupric dibromomethane diphosphonate, calcium dichloromethane diphosphonate, magnesium dichloromethane diphosphonate, barium dichloromethane diphosphonate, strontium dichloromethane diphosphonate, zinc dichloromethane diphosphonate, beryllium dichloromethane diphosphonate, cadmium dichloromethane diphosphonate, mercury dichloromethane diphosphonate, cupric dichloromethane diphosphonate, silver dichloromethane diphosphonate, auric dichloromethane diphosphonate, titanium dichloromethane diphosphonate, zirconium dichloromethane diphosphonate, stannous dichloromethane diphosphonate, stannic dichloromethane diphosphonate, chromic dichloromethane diphosphonate, tungsten dichloromethane diphosphonate, molybdenum dichloromethane diphosphonate, manganic dichloromethane diphosphonate, ferrous dichloromethane diphosphonate, ferric dichloromethane diphosphonate, cobaltous dichloromethane diphosphonate, nickelic dichloromethane diphosphonate, platinum dichloromethane diphosphonate, palladium dichloromethane diphosphonate, uranium dichloromethane diphosphonate, uranyl dichloromethane diphosphonate, cerium dichloromethane diphosphonate, hafnium dichloromethane diphosphonate, radium dichloromethane diphosphonate, plumbous dichloromethane diphosphonate, dimethyltin dichloromethane diphosphonate, dioctadecyltin dichloromethane diphosphonate, dibutyltin dichloromethane diphosphonate, di (p-tolyl) tin dichloromethane diphosphonate, monooctyltin dichloromethane diphosphonate, trihexyltin dichloromethane diphosphonate, ferric bromomethane triphosphonate, calcium chloromethane triphosphonate, magnesium chloromethane triphosphonate, beryllium chloromethane triphosphonate, strontium chloromethane triphosphonate, barium chloromethane triphosphonate, radium chloromethane triphosphonate, zinc chloromethane triphosphonate, cadmium chloromethane triphosphonate, mercury chloromethane triphosphonate, cupric chloromethane triphosphonate, silver chloromethane triphosphonate, aurous chloromethane triphosphonate, titanic chloromethane triphosphonate, zirconium chloromethane triphosphonate, plumbous chloromethane triphosphonate, stannous chloromethane triphosphonate, stannic chloromethane triphosphonate, chromic chloromethane triphosphonate, tungsten chloromethane triphosphonate, molybdenum chloromethane triphosphonate, manganous chloromethane triphosphonate, ferrous chloromethane triphosphonate, ferric chloromethane triphosphonate, cobaltic chloromethane triphosphonate, nickelous chloromethane triphosphonate, platinum chloromethane triphosphonate, palladium chloromethane triphosphonate, uranium chloromethane triphosphonate, uranyl chloromethane triphosphonate, cerium chloromethane triphosphonate, hafnium chloromethane triphosphonate, dibutyltin chloromethane triphosphonate, dioctyltin chloromethane triphosphonate, amyltin chloromethane triphosphonate, triethyltin chloromethane triphosphonate, di(o-tolyl) tin chloromethane triphosphonate, calcium methane triphosphonate, beryllium methane triphosphonate, magnesium methane triphosphonate, strontium methane triphosphonate, barium methane triphosphonate, radium methane triphosphonate, zinc methane triphosphonate, cadmium methane triphosphonate, mercury methane triphosphonate, cuprous methane triphosphonate, cupric methane triphosphonate, silver methane triphosphonate, auric methane triphosphonate, titanic methane triphosphonate, zirconic methane triphosphonate, plumbous methane triphosphonate, stannous methane triphosphonate, stannic methane triphosphonate, chromous methane triphosphonate, chromic methane triphosphonate, tungsten methane triphosphonate, molybdenum methane triphosphonate, manganous methane triphosphonate, manganic methane triphosphonate, ferrous methane triphosphonate, ferric methane triphosphonate, cobaltous methane triphosphonate, cobaltic methane triphosphonate, nickelous methane triphosphonate, nickelic methane triphosphonate, platinum methane triphosphonate, palladium methane triphosphonate, uranyl methane triphosphonate, hafnium methane triphosphonate, cerium methane triphosphonate, dibutyltin methane triphosphonate, dioctyltin methane triphosphonate, diphenyltin methane triphosphonate, dioctadecyltin methane triphosphonate, dimethyltin methane triphosphonate, di (m-tolyl) tin methane triphosphonate, monobutyltin methane triphosphonate, tributyltin methane triphosphonate, monooctyltin methane triphosphonate, trioctyltin methane triphosphonate, calcium methane tetraphosphonate, magnesium methane tetraphosphonate, barium methane tetraphosphonate, strontium methane tetraphosphonate, radium methane tetraphosphonate, zinc methane tetraphosphonate, cadmium methane tetraphosphonate, mercury methane tetraphosphonate, cuprous methane tetraphosphonate, cupric methane tetraphosphonate, silver methane tetraphosphonate, aurous methane tetraphosphonate, auric methane tetraphosphonate, titanic methane tetraphosphonate, zirconic methane tetraphosphonate, plumbous methane tetraphosphonate, stannous methane tetraphosphonate, stannic methane tetraphosphonate, chromous methane tetraphosphonate, chromic methane tetraphosphonate, beryllium methane tetraphosphonate, tungsten methane tetraphosphonate, molybdenum methane tetraphosphonate, manganous methane tetraphosphonate, manganic methane tetraphosphonate, ferrous methane tetraphosphonate, ferric methane tetraphosphonate, cobaltous methane tetraphosphonate, cobaltic methane tetraphosphonate, nickelous methane tetraphosphonate, nickelic methane tetraphosphonate, platinum methane tetraphosphonate, palladium methane tetraphosphonate, uranium methane tetraphosphonate, uranyl methane tetraphosphonate, hafnium methane tetraphosphonate, cerium methane tetraphosphonate, niobium methane tetraphosphonate, dibutyltin methane tetraphosphonate, dioctyltin methane tetraphosphonate, monobutyltin methane tetraphosphonate, tributyltin methane tetraphosphonate, diphenyltin methane tetraphosphonate, calcium phenyl methane diphosphonate, barium phenyl methane diphosphonate, magnesium phenyl methane diphosphonate, beryllium phenyl methane diphosphonate, zinc phenyl methane diphosphonate, cadium phenyl methane diphosphonate, mercury phenyl methane diphosphonate, cupric phenyl methane diphosphonate, silver phenyl methane diphosphonate, auric phenyl methane diphosphonate, titanium phenyl methane diphosphonate, zirconium phenyl methane diphosphonate, stannous phenyl methane diphosphonate, stannic phenyl methane diphosphonate, chromic phenyl methane diphosphonate, tungsten phenyl methane diphosphthalate, molybdenum phenyl methane diphosphonatem manganese phenyl methane diphosphonate, ferrous phenyl methane diphosphonate, ferric phenyl methane diphosphonate, cobaltic phenyl methane diphosphonate, nickelous phenyl methane diphosphonate, platinum phenyl methane diphosphonate, palladium phenyl methane diphosphonate, uranium phenyl methane diphosphonate, uranyl phenyl methane diphosphonate, plumbous phenyl methane diphosphonate, hafnium phenyl methane diphosphonate, cerium phenyl methane diphosphonate, dibutyltin phenyl metahne diphosphonate, monobutyltin phenyl methane diphosphonate, tributyltin phenyl methane diphosphonate, dioctyltin phenyl methane diphosphonate, diphenyltin phenyl methane diphosphonate, calcium phenyl methane triphosphonate, magnesium phenyl methane triphosphonate, beryllium phenyl methane triphosphonate, strontium phenyl methane triphosphonate, barium phenyl methane triphosphonate, radium phenyl methane triphosphonate, zinc phenyl methane triphosphonate, cadmium phenyl methane triphosphonate, mercury phenyl methane triphosphonate, cupric phenyl methane triphosphonate, silver phenyl methane triphosphonate, aurous phenyl methane triphosphonate, titanic phenyl methane triphosphonate, zinconium phenyl methane triphosphonate, plumbous phenyl methane triphosphonate, stannous phenyl methane triphosphonate, stannic phenyl methane triphosvinyl hydroxymethane diphosphonate, cadmium isopropyl hydroxymethane diphosphonate, mercury vinyl hydroxymethane diphosphonate, mercury isopropenyl hydroxymethane diphosphonate, cupric vinyl hydroxymethane diphosphonate, cupric isopropenyl hydroxymethane diphosphonate, silver vinyl hydroxymethane diphosphonate, silver isopropenyl hydroxymetahne diphosphonate, suric vinyl hydroxymethane diphosphonate, suric isopropenyl hydroxymethane diphosphonate, titanium vinyl hydroxymethane diphosphonate, titanium isopropenyl hydroxymethane diphosphonate, zirconium vinyl hydroxymethane diphosphonate, sirconium isopropenyl hydroxymethane diphosphonate, stannous vinyl hydroxymethane diphosphonate, stannic vinyl hydroxymethane diphosphonate, chromic vinyl hydroxymethane diphosphonate, tungsten vinyl hydroxymethane diphosphonate, molybdenum vinyl hydroxymethane diphosphonate, manganese vinyl hydroxymethane diphosphonate, ferrous vinyl hydroxymethane diphosphonate, ferric vinyl hydroxymethane diphosphonate, cobaltic vinyl hydroxymethane diphosphonate, nickelous vinyl hydroxymethane diphosphonate, platinum vinyl hydroxymethane diphosphonate, palladium vinyl hydroxymethane diphosphonate, uranium vinyl hydroxymethane diphosphonate, uranyl vinyl hydroxymethane diphosphonate, plumbous vinyl hydroxymethane diphosphonate, hefnium vinyl hydroxymethane diphosphonate, cerium vinyl hydroxymethane diphosphate, calcium chloromethyl hydroxymethane diphosphate, calcium dichloromethyl hydroxymethane diphosphate, calcium trichloromethyl hydroxymethane diphosphate, calcium chloroethyl hydroxymethane diphosphate, barium chloromethyl hydroxymethane diphosphate, magnesium chloromethyl hydroxymethane diphosphate, beryllium chloromethyl hydroxymethane diphosphate, zinc chloromethyl hydroxymethane diphosphonate, cadmium chloromethyl hydroxymethane diphosphonate, mercury chloromethyl hydroxymethane diphosphonate, cupric chloromethyl hydroxymethane diphosphonate, silver chloromethyl hydroxymethane diphosphonate, curic chloromethyl hydroxymethane diphosphonate, titanium chloromethyl hydroxymethane diphosphonate, zirconium chloromethyl hydroxymethane diphosphonate, stannous chlormethyl hydroxymethane diphosphonate, stannic chloromethyl hydroxymethane diphosphonate, chromic chloromethyl hydroxymethane diphosphonate, tungsten chloromethyl hydroxymethane diphosphonate, molybdenum chloromethyl hydroxymethane diphosphonate, manganous chloromethyl hydroxymethane diphosphonate, ferrous chloromethyl hydroxymethane diphosphonate, ferric chloromethyl hydroxymethane disphosphonate, cobaltic chloromethyl hydroxymethane diphosphonate, nickelous chloromethyl hydroxymethane diphosphonate, platinum chloromethyl hydroxymethane diphosphonate, palladium chloromethyl hydroxymethane diphosphonate, uranium chloromethyl hydroxymethane diphosphonate, uranyl chloromethyl hydroxymethane diphosphonate, plumbous chloromethyl hydroxymethane diphosphonate, hafnium chloromethyl hydroxymethane diphosphonate, cerium chloromethyl hydroxymethane diphosphonate, calcium phenyl hydroxymethane diphosphonate, calcium naphthyl hydroxymethane diphosphonate, barium phenyl hydroxymethane diphosphonate, magnesium phenyl hydroxymethane diphosphonate, beryllium phenyl hydroxymethane diphosphonate, zinc phenyl hydroxymethane diphosphonate, cadmium phenyl hydroxymethane diphosphonate, mercury phenyl hydroxymethane diphosphonate, cupric phenyl hydroxymethane diphosphonate, silver phenyl hydroxymethane diphosphonate, suric phenyl hydroxymethane diphosphonate, titanium phenyl hydroxymethane diphosphonate, zirconium phenyl hydroxymethane diphosphonate, stannous phenyl hydroxymethane diphosphonate, stannic phenyl hydroxymethane diphosphonate, chromic phenyl hydroxymethane diphosphonate, tungsten phenyl hydroxymethane diphosphonate, molybdenum phenyl hydroxymethane diphosphonate, manganous phenyl hydroxymethane diphosphonate, ferrous phenyl hydroxymethane diphosphonate, ferric phenyl hydroxymethane diphosphonate, cobaltic phenyl hydroxymethane diphosphonate, nickelous phenyl hydroxymethane diphosphonate, platinum phenyl hydroxymethane diphosphonate, palladium phenyl hydroxymethane diphosphonate, uranium phenyl hydroxymethane diphosphonate, uranyl phenyl hydroxymethane diphosphonate, plumbous phenyl hyroxymethane diphsophonate, hafnium phenyl hydroxymethane diphosphonate, cerium phenyl hydroxymethane diphosphonate, calcium chlorophenyl hydroxymethane diphosphonate, calcium trichlorophenyl hydroxymethane diphosphonate, barium chlorophenyl hydroxymethane diphosphonate, magnesium chlorophenyl hydroxymethane diphosphonate, baryllium chlorophenyl hydroxymethane diphosphonate, zinc chlorophenyl hydroxymethane diphosphonate, cadmium chlorophenyl hydroxymethane diphosphonate, mercury chlorophenyl hydroxymethane diphosphonate, cupric chlorophenyl hydroxymethane, diphosphonate, silver chlorophenyl hydroxymethane diphosphonate, suric chlorophenyl hydroxymethane diphosphonate, titanium chlorophenyl hydroxymethane diphosphonate, zirconium chlorphenyl hydroxymethane diphosphonate, stannous chlorophenyl hydroxymethane diphosphonate, stannic chlorophenyl hydroxymethane diphosphonate, chromic chlorophenyl hydroxymethane diphosphonate, tungsten chlorophenyl hydroxymethane diphosphonate, molybdenum chlorophenyl hydroxymethane diphosphonate, manganous chlorphenyl hydroxymethane diphosphonate, ferrous chlorophenyl hydroxymethane diphosphonate, ferric chlorophenyl hydroxymethane diphosphonate, cobaltic chlorophenyl hydroxymethane diphosphonate, nickelous chlorphenyl, hydroxymethane diphosphonate, platinum chlorophenyl hydroxymethane diphosphonate, palladium chlorophenyl hydroxymethane diphosphonate, uranium chlorphenyl hydroxymethane diphosphonate, uranyl chlorophenyl hydroxymethane diphosphonate, plumbous chlorophenyl hydroxymethane diphosphonate, hafnium chlorophenyl hydroxymethane diphosphonate, cerium chlorophenyl hydroxymethane diphosphonate, calcium chloro hydroxymethane diphosphonate, calcium bromo hydroxymethane diphosphonate, barium chloro hydroxymethane diphosphonate, magnesium chloro hydroxymethane diphosphonate, baryllium chloro hydroxymethane diphosphonate, zinc chloro hydroxymethane diphosphonate, cadmium chloro hydroxymethane diphosphonate, mercury chloro hydroxymethane diphosphonate, cupric chloro hydroxymethane diphosphonate, silver chloro hydroxymethane diphosphonate, curic chloro hydroxymethane diphosphonate, titanium chloro hydroxymethane diphosphonate, zirconium chloro hydroxymethane diphosphonate, stannous chloro hydroxymethane diphosphonate, stannic chloro hydroxymethane diphosphonate, chromic chloro hydroxymethane diphosphonate, tungsten chloro hydroxymethane diphosphonate, molybdenum chloro hydroxymethane diphosphonate, manganese chloro hydroxymethane diphosphonate, ferrous chloro hydroxymethane diphosphonate, ferric chloro hydroxymethane diphosphonate, cobaltic chloro hydroxymethane diphosphonate, nickelous chloro hydroxymethane diphosphonate, platinum chloro hydroxymethane diphosphonate, palladium chloro hydroxymethane diphosphonate, uranium chloro hydroxymethane diphosphonate, uranyl chloro hydroxymethane diphosphonate, plumbous chloro hydroxymethane diphosphonate, hafnium chloro hydroxymethane diphosphonate, cerium chloro hydroxymethane diphosphonate, clacium chloromethyl chloromethane diphosphonate, barium chloromethyl chloromethane diphosphonate, magnesium chloromethyl chloromethane diphosphonate, zinc chloromethyl chloromethane diphosphonate, ferric chloromethyl chloromethane diphosphonate, cadmium chloromethyl chloromethane diphosphonate, calcium chlorophenyl chloromethane diphosphonate, barium chlorophenyl chloromethane diphosphonate, zinc chlorophenyl chloromethane diphosphonate, magnesium chlorophenyl chloromethane diphosphonate, ferric chlorophenyl chloromethane diphosphonate, ferrous chlorophenyl chloromethane diphosphonate, calcium phenyl chloromethane diphosphonate, barium phenyl chloromethane phonate, chromic phenyl methane triphosphonate, tungsten phenyl methane triphosphonate, molybdenum phenyl methane triphosphonate, manganous phenyl methane triphosphate, ferrous phenyl methane triphosphonate, ferric phenyl methane triphosphonate, cobaltic phenyl methane triphosphonate, nickelous phenyl methane triphosphonate, platinum phenyl methane triphosphonate, palladium phenyl methane triphosphonate, uranium phenyl methane triphosphonate, uranyl phenyl methane triphosphonate, cerium phenyl methane triphosphonate, hafnium phenyl methane triphosphonate, dibutyltin phenyl methane triphosphonate, dioctyltin phenyl methane triphosphonate, amyltin phenyl methane triphosphonate, triethyltin phenyl methane triphosphonate, di (o-tolyl) tin phenyl methane triphosphonate, calcium hydroxymethane diphosphonate, barium hydroxymethane diphosphonate, magnesium hydroxymethane diphosphonate, beryllium hydroxymethane diphosphonate, zinc hydroxymethane diphosphonate, cadmium hydroxymethane diphosphonate, mercury hydroxymethane diphosphonate, cupric hydroxymethane diphosphonate, silver hydroxymethane diphosphonate, auric hydroxymethane diphosphonate, titanium hydroxymethane diphosphonate, zirconium hydroxymethane diphosphonate, stannous hydroxymethane diphosphonate, stannic hydroxymethane diphosphonate, chromic hydroxymethane diphosphonate, tungsten hydroxymethane diphosphonate, molybdenum hydroxymethenae diphosphonate, manganous hydroxymethane diphosphonate, ferrous hydroxymethane diphosphonate, ferric hydroxymethane diphosphonate, cobaltic hydroxymethane diphosphonate, nickelous hydroxmethane diphosphonate, platinum hyroxymethane diphosphonate, palladium hydroxymethane diphosphonate, uranium hydroxymethane diphosphonate, uranyl hydroxymethane diphosphonate, plumbous hydroxymethane diphosphonate, hafnium hydroxymethane diphosphonic cerium hydroxymethane diphosphonate, dibutyltin hydroxymethane diphosphonate, calcium methyl hydroxymethane diphosphonate, calcium ethyl hydroxymethane diphosphonate, calcium butyl hydroxymethane diphosphonate, calcium hexyl hydroxymethane diphosphonate, calcium decyl hydroxymethane diphosphonate, calcium pentadecyl hydroxymethane diphosphonate, barium methyl hydroxymethane diphosphonate, barium butyl hydroxymethane diphosphonate, barium hexyl hydroxymethane diphosphonate, magnesium methyl hydroxymethane diphosphonate, magnesium butyl hydroxymethane diphosphonate, magnesium heptyl hydroxymethane diphosphonate, zinc methyl hydroxymethane diphosphonate, beryllium methyl hydroxymethane diphosphonate, cadmium methyl hydroxymethane diphosphonate, mercury methyl dihydroxymethane diphosphonate, cupric methyl hydroxymethane diphosphonate, silver methyl hydroxymethane diphosphonate, auric methyl hydroxymethane diphosphonate, titanium methyl hydroxymethane diphosphonate, zirconium methyl hydroxymethane diphosphonate, stannous methyl hydroxymethane diphosphonate, stannic methyl hydroxymethane diphosphonate, chromic methyl hydroxymethane diphosphonate, tungsten methyl hydroxymethane diphosphonate, molybdenum methyl hydroxymethane diphosphonate, manganous methyl hydroxymethane diphosphonate, ferrous methyl hydroxymethane diphosphonate, ferric methyl hydroxymethane diphosphonate, cobaltic methyl hydroxymethane diphosphonate, nickelous methyl hydroxymethane diphosphonate, platinum methyl hydroxymethane diphosphonate, palladium methyl hydroxymethane diphosphonate, uranium methyl hydroxymethane diphosphonate, uranyl methyl hydroxymethane diphosphonate, plumbous methyl hydroxymethane diphosphonate, hafnium methyl hydroxymethane diphosphonate, cerium methyl hydroxymethane diphosphonate, calcium vinyl hydroxymethane diphosphonate, calcium isopropenyl hydroxymethane diphosphonate, barium vinyl hydroxymethane diphosphonate, barium isopropenyl hydroxymethane diphosphonate, magnesium vinyl hydroxymethane diphosphonate, magnesium isopropenyl hydroxymethane diphosphonate, beryllium vinyl hydroxymethane diphosphonate, beryllium isopropenyl hydroxymethane diphosphonate, zinc vinyl hydroxymethane diphosphonate, zinc isopropenyl hydroxymethane diphosphonate, cadmium diphosphonate, magnesium phenyl chloromethane diphosphonate, calcium methyl chloromethane diphosphonate, barium methyl chloromethane diphosphonate, magnesium methyl chloromethane diphosphonate, calcium diphenylmethane diphosphonate, barium diphenylmethane diphosphonate, magnesium diphenylmethane diphosphonate, calcium vinyl chloromethane diphosphonate, calcium phenyl methyl methane diphosphonate, calcium vinyl phenyl methane diphosphonate, calcium chlorophenyl methyl methane diphosphonate, calcium chlorophenyl phenyl methane diphosphonate.

The chelated salt or the complex formed by the chelating action is useful as a source of the metal chelated. The chelated metal can be received from the complex, for example, by driving off the solvent or the liquid medium in which the complex is present. The chelated metal can then be won by flushing the solid complex with a strong acid or base such as nitric acid, hydrochloric acid, potassium hydroxide and sodium hydroxide. Concentrated nitric acid is the preferred reagent for this purpose. The acid will serve to regenerate the polyphosphonic acid chelating agent from the complex at the same time precipitate out the metal, e.g. as cupric nitrate, silver nitrate and uranium chloride, etc. Subsequent purification and recovery steps will follow substantially the known method.

The complexes found by the chelating agents with the chelated metal ions are themselves useful and valuable products. Thus, for example, the lead salts or chelates of the polyphosphonic acids of the invention are excellent pigments and also are useful as polyvinyl chloride stabilizers. These lead salts or chelates can be prepared, for example, by adding a dilute solution of lead acetate to a polyphosphonic acid such as hydroxy methanediphosphonic acid. Another example is furnished by the dibutyltin derivatives of the polyphosphonic acids which are also polyvinyl chloride stabilizers.

EXAMPLE 25

A 5% aqueous solution of lead acetate containing about 26.6 grams of lead acetate (0.1 mole) was thoroughly mixed with 41.2 grams of hydroxymethyl methanediphosphonic acid. Upon mixing and sitting, the mixture expanded about 50 fold in volume and resulted in a gelatinous solid. This gelatinous solid was found to be an excellent pigment for paints, etc.

About 50 grams of the gelatinous solid containing the lead chelate and made as above were mixed with 450 grams of an oleo resinous clear varnish. This mixture was found to be an excellent material for protectively coating wood, metals, etc. The lead chelate served as the pigment which had very high surface coverage power.

EXAMPLES 26–46

In the following examples, the chelating power of many of the polyphosphonic acids and their salts of the invention was determined as follows:

The chelating agent was first dissolved in kerosene to obtain a 5% solution and this solution was then thoroughly mixed with an aqueous solution containing the metal ions to be chelated in theform of the nitrate. The mixing was sufficient to insure intimate contact between the chelating agent and the metal ions. The pH of the aqueous phase was adjusted by the use of sodium hydroxide. After the thorough mixing, the mixture was allowed to stand and separate into two phases. Thereafter, the organic phase was physically separated from the aqueous phase. The kerosene solvent was then driven off from the organic phase by heating and the remaining solid burned to obtain the metal chelated in its oxide form. An excess of metal ions was used in the aqueous phase to insure exhaustion of the chelating agent. The metal oxide thus obtained was then weighed and the result was converted to amount of metal so found. The results of these experiments are tabulated below.

TABLE I

| Example No. | Metal Ion Chelated | Chelating Agent | pH | Amount of Metal Chelated mg/gm of Chelator |
|---|---|---|---|---|
| 26 | Fe** | Phenyl methane diphosphonic acid | 7 | 371 |
| 27 | Fe** | Phenyl methane diphosphonic acid | 11 | 252 |
| 28 | Pb** | Phenyl methane diphosphonic acid | 8 | 241 |
| 29 | Hg** | Phenyl methane diphosphonic acid | 8 | 199 |
| 30 | Co** | Phenyl methane diphosphonic acid | 8 | 195 |
| 31 | Zn** | Phenyl methane diphosphonic acid | 8 | 124 |
| 32 | Cu** | Phenyl methane diphosphonic acid | 7 | 199 |
| 33 | Fe*** | Phenyl methane triphosphonic acid | 7 | 530 |
| 34 | Fe*** | Phenyl methane triphosphonic acid | 11 | 359 |
| 35 | Pb** | Phenyl methane triphosphonic acid | 8 | 344 |
| 36 | Hg** | Phenyl methane triphosphonic acid | 8 | 284 |
| 37 | Co** | Phenyl methane triphosphonic acid | 8 | 279 |
| 38 | Zn** | Phenyl methane triphosphonic acid | 8 | 177 |
| 39 | Cu** | Phenyl methane triphosphonic acid | 7 | 284 |
| 40 | Fe*** | Methane tetra-phosphonic acid | 7 | 586 |
| 41 | Fe*** | Methane tetra-phosphonic acid | 11 | 398 |
| 42 | Pb** | Methane tetra-phosphonic acid | 8 | 381 |
| 43 | Hg** | Methane tetra-phosphonic acid | 8 | 314 |
| 44 | Co** | Methane tetra-phosphonic acid | 8 | 309 |
| 45 | Zn** | Methane tetra-phosphonic acid | 8 | 196 |
| 46 | Cu** | Methane tetra-phosphonic acid | 7 | 314 |

Although kerosene was used as the solvent in Examples 26–46 above, other aliphatic or aromatic solvents can be used. Examples of other suitable solvents are naphtha, hexane, octane, decalin, tetralin, petroleum ether, toluene and xylene, etc.

In above Examples 26–46, an excess of metal ions was used to determine the chelating capacity of the chelating agents. When the chelating agents are used in actual processes, such as in textile treatment or in the recovery of valuable metals like gold and uranium, a 5 percent excess of the chelating agents is preferably employed to insure the sequestering of all of the metal ions present. It is not necessary to use more than 5 percent excess of the chelators.

In Examples 26 to 39 above, the chelating polyphosphonic acids employed contain a phenyl radical to make the chelator more selectively soluble in the organic phase. When a chelating agent is to be employed in an aqueous system, such as is commonly the case in treating textile materials, then it is preferable to have a hydroxyl group in place of or in addition to the phenyl radical to impart solubility therein.

When the results of Examples 26 and 27 are compared, it is apparent that for a given chelating agent the chelating capacity is incresed when the pH is lowered. This rule is generally true for most known chelators.

EXAMPLE 47

About 10 g. of methyl hydroxymethane diphosphonic acid was dissolved in 190 g. of petroleum ether and the solution was then thoroughly mixed with an aqueous solution of ferric nitrate. A large excess of ferric ions was employed. After the thorough mixing, the mixture was allowed to stand and separate into two phases. Thereafter the organic phase was physically separated from the aqueous phase. The petroleum ether solvent was driven off from the organic phase and the solid chelated salt was found to contain iron. However, the amount of iron present in chelated salt was relatively small when compared to the results of Examples 26 and 27. This is probably due to the presence of a hydroxyl group on the central carbon atoms in the chelating diphosphonic acid, which imparted solubility to the chelated salt in the aqueous phase.

EXAMPLES 48-57

Example 47 was repeated except that the chelating agent was replaced as follows:

TABLE II

| Example No. | Chelating Agent | Chelated Salt Found |
|---|---|---|
| 48 | Hydroxymethane diphosphonic acid | Ferric hydroxymethane diphosphonate |
| 49 | Hydroxymethane triphosphonic acid | Ferric hydroxymethane triphosphonate |
| 50 | Hydroxy chloromethane diphosphonic acid | Ferric hydroxy chloromethane diphosphonate |
| 51 | Chloromethyl hydroxymethane diphosphonic acid | Ferric chloromethyl hydroxymethane diphosphonate |
| 52 | Methyl hydroxymethane diphosphonic acid | Ferric methyl hydroxymethane diphosphonate |
| 53 | Chloro hydroxymethane diphosphonic acid | Ferric chloro hydroxymethane diphosphonate |
| 54 | Vinyl hydroxymethane diphosphonic acid | Ferric vinyl hydroxymethane diphosphonate |
| 55 | Dichloromethane diphosphonic acid | Ferric dichloromethane diphosphonate |
| 56 | Chloromethane triphosphonate acid | Ferric chloromethane triphosphonate |
| 57 | Dibutyltin methane diphosphonic acid | Ferric dibutyltin methane diphosphonate |

The concentration of the chelating agents which can be suitably employed in the present invention can be varied within a wide range. In general, the concentration of the chelating solution to be used depends on the amount of metal ions to be sequestered and on the solubility of the chelator in the system. I have found that solutions containing between 0.1% to 50% by weight of the chelator are particularly suitable although the chelating agents can be used in an amount of 75% or more of the total solution. The chelated metal complex produced by the reaction of the chelating agent with the metal ion is useful as resin stabilizer. This is particularly true of lead, barium, cadmium, tin and calcium chelate. When used as resin stabilizer the chelated metal complex or metal chelate can be used in an amount of about 0.01% to about 10-15% by weight of the resin. The use of chelated metal complex as resin stabilizer is illustrated by the following example:

EXAMPLE 58

One mole of phenyl hydroxy methane diphosphonic acid was reacted with 2 moles of barium oxide to obtain the barium salt of phenyl hydroxymethane diphosphonic acid. This salt or chelate was then incorporated into a polyvinyl chloride resin formula as follows:

| PVC resin | 100 grams |
|---|---|
| Dioctyl phthalate | 50 grams |
| Barium salt of phenyl hydroxymethane diphosphonic acid | 2 grams |

The dioctyl phthalate is employed as a plasticizer for the resin.

The above formula was thoroughly mixed and milled at 330° F. into a plastic film. The film was then oven aged for 30 minutes at 325° F. After the oven aging the film was essentially colorless and transparent.

When the above resin mixture was repeated but without the use of the barium salt, the resultant film was charred and turned completely black after the same oven aging.

Corresponding cadmium, zinc, strontium, tin and lead salts were also prepared and they were found to possess similar ability to prevent the decomposition and discoloration of chlorinated resins. This was also true of the dioctyltin and dibutyltin chelates of phenyl hydroxymethane diphosphonic acid.

The novel stabilizers of the present invention can be used with halogen containing vinyl and vinylidene resins in which the halogen is attached directly to a carbon atom in the polymer chain. Preferably, the resin is a vinyl halide resin, specifically, a vinyl chloride resin. Usually, the vinyl chloride resin is made from monomers consisting of vinyl chloride alone or a mixture of monomers comprising at least 70% vinyl chloride by weight. When vinyl chloride copolymers are stabilized, preferably the copolymer of vinyl chloride with an ethylenically unsaturated compound copolymerizable therewith contains at least 10% of polymerized vinyl chloride.

As the chlorinated resin there can be employed chlorinated polyethylene having 14 to 75%, e.g., 27% chlorine by weight, polyvinyl chloride, polyvinylidene chloride, polyvinyl bromide, polyvinyl fluoride, copolymers of vinyl chloride with 1 to 90%, preferably 1 to 30%, of a copolymerizable ethylenically unsaturated material such as vinyl acetate, vinyl butyrate, vinyl benzoate, vinylidene chloride, diethyl fumarate, diethyl maleate, other alkyl fumarates and maleates, vinyl propionate, methyl acrylate, 2-ethylhexyl acrylate, butyl acrylate and other alkyl acrylates, methyl metacrylate, ethyl methacrylate, butyl methacrylate and other alkyl methacrylates, methyl alpha chloroacrylate, styrene, trichloroethylene, vinyl ethers such as vinyl ethyl ether, vinyl chloroethyl ether and vinyl phenyl ether, vinyl ketones such as vinyl methyl ketone and vinyl phenyl ketone, 1-fluoro-1-chloroethylene, acrylonitrile, chloroacrylonitrile, allylidene diacetate and chloroallylidene diacetate. Typical copolymers include vinyl chloride-vinyl acetate (96:4 sold commercially as VYNW), vinyl chloride-vinylacetate(87:13), vinyl chloride-vinyl acetate-maleic anhydride (86:13:1), vinyl chlorine-vinylidene chloride (95:5), vinyl chloride-diethyl fumarate (95:5), vinyl chloride-trichloroethylene (95:5), vinyl chloride-2-ethylhexyl acrylate (80:20).

The stabilizers of the present invention can be incorporated with the resin by admixing in an appropriate mill or mixer or by any of the other well-known methods which provide for uniform distribution throughout the resin compositions. Thus, mixing can be accomplished by milling on rolls at 100°-160° C.

In addition to the novel stabilizers there can also be incorporated with the resin conventional additives such as plasticizers, pigments, fillers, dyes, ultraviolet light absorbing agents, densifying agents and the like.

If a plasticizer is employed, it is used in conventional amount, e.g., 30 to 150 parts per 100 parts of resin. Typical plasticizers are di-2-ethylhexyl phthalate, dibutyl sebacate dioctyl sebacate, tricresyl phosphate, butyl phthalyl butyl glycolate.

Although several of the uses of the chelating agents of the invention are specifically given and illustrated by examples, it is to be understood that the usefulness of the present chelators is not limited thereto. Other uses of chelating agents are known in the art and a short review of these uses are given by Taylor in his article in the Oct. 20, 1956 issue of Chemistry and Industry at pp. 1134–1135.

What is claimed is:

1. A process for chelating gold, silver, or uranium ions comprising contacting said metal ions with a phosphorus chelating compound having the formula

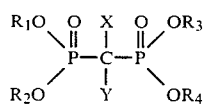

where $R_1$, $R_2$, $R_3$, and $R_4$ are selected from the group consisting of hydrogen, alkali metals, and ammonium, and X is alkyl and Y is hydroxyl.

2. A process according to claim 1 wherein X is alkyl of 1 to 19 carbon atoms.

3. A process according to claim 2 where X is alkyl of 1 to 5 carbon atoms.

4. A process according to claim 3 where X is methyl.

5. A process according to claim 4 wherein there are chelated uranium ions.

6. A process according to claim 3 wherein there are chelated uranium ions.

7. A process according to claim 2 wherein there are chelated uranium ions.

8. A process according to claim 1 wherein there are chelated uranium ions.

9. A process acccording to claim 8 wherein the uranium is in the form of the uranyl group.

10. A process according to claim 7 wherein the uranium is in the form of the uranyl group.

11. A process according to claim 6 wherein the uranium is in the form of the uranyl group.

12. A process according to claim 5 wherein the uranium is in the form of the uranyl group.

13. A process according to claim 4 wherein the uranium is in the form of the uranyl group.

14. Uranium methyl hydroxymethane diphosphonate.

15. Uranyl methyl hydroxymethane diphosphonate.

16. A compound having the formula

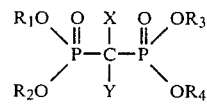

where at least one of $R_1$, $R_2$, $R_3$, and $R_4$ is gold, silver, uranium, or uranyl and the balance of $R_1$, $R_2$, $R_3$, and $R_4$ are hydrogen, alkali metal, or ammonium, X is alkyl and Y is hydroxyl.

17. A compound according to claim 16 where X is methyl.

* * * * *